US009963489B2

(12) United States Patent
Valenta et al.

(10) Patent No.: US 9,963,489 B2
(45) Date of Patent: May 8, 2018

(54) HOUSE DUST MITE ALLERGEN

(71) Applicant: Biomay AG, Vienna (AT)

(72) Inventors: Rudolf Valenta, Theresienfeld (AT); Margit Weghofer, Vienna (AT); Susanne Vrtala, Vienna (AT); Friedrich Horak, Innermanzing (AT); Peter Valent, Vienna (AT); Stefan Florian, Munich (DE)

(73) Assignee: BIOMAY AG, Vienna (AT)

( * ) Notice: Subject to any disclaimer, the term of this patent is extended or adjusted under 35 U.S.C. 154(b) by 0 days. days.

(21) Appl. No.: 15/381,209

(22) Filed: Dec. 16, 2016

(65) Prior Publication Data

US 2017/0218034 A1    Aug. 3, 2017

Related U.S. Application Data

(60) Division of application No. 14/468,499, filed on Aug. 26, 2014, now abandoned, which is a continuation of application No. 12/298,901, filed as application No. PCT/AT2007/000201 on Apr. 27, 2007, now abandoned.

(30) Foreign Application Priority Data

Apr. 28, 2006 (AT) .................................. 733/2006

(51) Int. Cl.
| | |
|---|---|
| *A61K 38/00* | (2006.01) |
| *A61K 39/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *C12N 11/00* | (2006.01) |
| *C12N 11/16* | (2006.01) |
| *C07K 14/435* | (2006.01) |
| *C07K 17/08* | (2006.01) |
| *G01N 33/68* | (2006.01) |

(52) U.S. Cl.
CPC ........ *C07K 14/43531* (2013.01); *C07K 17/08* (2013.01); *G01N 33/6854* (2013.01); *G01N 33/6893* (2013.01); *G01N 2333/43582* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 9,308,251 B2* | 4/2016 | Niespodziana | ........ A61K 39/36 |
| 2004/0123343 A1 | 6/2004 | La Rosa et al. | |
| 2006/0048240 A1 | 3/2006 | Alexandrov et al. | |
| 2006/0084794 A1 | 4/2006 | Rosen et al. | |
| 2006/0150283 A1 | 7/2006 | Alexandrov | |
| 2010/0037355 A1 | 2/2010 | Alexandrov et al. | |

FOREIGN PATENT DOCUMENTS

| | | |
|---|---|---|
| EP | 1 612 219 | 1/2006 |
| JP | 2006-14726 | 1/2006 |
| WO | 2004/003009 | 1/2004 |

OTHER PUBLICATIONS

Hiller et al. 'Microarrayed alleregn molecules:diagnostic gatekeepers for allergy treatment.' The FASEB Journal express article 10.1096/fj.01-0711fje. Published online Jan. 14, 2002.*
Freydank et al. 'Protein structure modeling indicates hexahistidine-tag interference with enzyme activity.' Proteins 72:173-183, 2008.*
Weghofer et al. "Identification of Der p 23, a Peritrophin-like Protein, as a New Major Dermatophagoides pteronyssinus Allergen Associated with the Peritrophic Matrix of Mite Fecal Pellets." J. Immunol. 190:3059-3067, 2013.
Ngo et al. "Computational Complexity, Protein Structure Prediction, and the Levinthal Paradox". The Protein Folding Problem and Tertiary Structure Prediction. Ed. K. Merz and S. Le Grand. Boston: Birkhauser, 1994, 491-495.
Blumenthal, et al., "Definition of an Allergen." Allergens and Allergen Immunotherapy. Ed. R Lockey, S. Bukantz and J. Bousquet. New York:Marcel Decker, 2004-37-50.
Skolnick, et al. "From genes to protein structure and function: novel applications of computational approaches in the genomic era." Trends in Biotech. 18:34-39, 2000.
Attwood, et al. 'The Babel of Bioinformatics.' Science. 290(5491):471-473, 2000.
Kuby, et al., 'Immunology.' Fourth Edition, Chapter 18:449-465.
Xu, et al., "The Genome of Cryptosporidium Hominis" Nature (2004), pp. 1107-1112.
Heymann, P.W. et al., Antigenic and structural analysis or group II allergens (Der fII and Der p lI) from house dust mites (*Dermatophagoides* spp) 1989 J. Allergy Clin. Immunol. 1055-1067.
Lin, K-L, et al., "Characterization of Dr p V allergen, cDna analysis, and IgE-mediated reactivity to the recombinant protein," 1994 J. Allergy Clin. Immunol. 989-998.
Takai, T., et al., "Determination of the N- and C-Terminal Sequences Required to Bind Human IgE of the Major House Dust Mite Allergen Der f 2 and Epitope Mapping for Monoclonal Antibodies," 1997 Molecular Immunology 34;3 pp. 255-261.
Pittner, G., et al., "Component-resolved diagnosis of house-dust mite allergy with purified natural and recombinant mite allergens," Clin Exp Allergy (2004), 34:597-603.
Vrtala, S., et al., "Strategies for converting allergens into hypoallergenic vaccine candidates," Methods (2004) 32:313-320.
Weghofer, M., et al., "Comparison of purified Dermatophagoides pteronyssinus allergens and extract by two-dimensional immunoblotting and quantitative immunoglobulin E inhibitions," Clin Exp Allergy (2005), 35:1384-1391.

(Continued)

*Primary Examiner* — Nora Rooney
(74) *Attorney, Agent, or Firm* — Oblon, McClelland, Maier & Neustadt, L.L.P.

(57) ABSTRACT

An immobilized polypeptide including a polypeptide bound to a surface of a polypeptide array or a chip, wherein the polypeptide has the amino acid sequence of SEQ ID NO:1, SEQ ID NO:3, SEQ ID NO:1 lacking the N-terminal methionine, SEQ ID NO:3 lacking the N-terminal methionine, or a combination thereof.

5 Claims, 6 Drawing Sheets

(56) References Cited

OTHER PUBLICATIONS

Metzler et all Solution structure of human CTLA-4 and delineation of a CD80/CD86 binding site conserved in CD28. o Nature Structural Biol. 4:527-531, 1997.
Brenner S. 'Errors in genome annotation.' Trends in Genetics 15:132-133, 1999.
Bowie et al. Deciphering the Message in Protein Sequences: Tolerance to Amino Acid Substitutions. Science 247:1306-1310, 1990.
Blumenthal et al. 'Definition of an allergen,' Allergens and Allergen Immunotherapy. Ed. R. Lockey, S. Bukantzand J. Bousquet. New York: Marcel Decker, 2004, pp. 373-50.
Schein et al. 'Bioinformatics Approaches to Classifying Allergens and Predicting Cross-Reactivity.' Immunol. Allergy. Clin. North Am. 27(1):1-27, 2007.
Friedl-Hajek et al. Clin. Exp. Allerg. 29:478-487, 1999.

\* cited by examiner

```
                                                        c a
  3 atatttctgcttgttttgaaa ATG AAA TTC AAC ATA ATC ATC
                           M   K   F   N   I   I   I   7
 47 GTT TTT ATT TCG TTG GCC ATT TTG GTC CAT TCA TCA TAT
     V   F   I   S   L   A   I   L   V   H   S   S   Y  20
 86 GCC GCC AAT GAT AAT GAT GAT GAT CCT ACC ACA ACC GTT
     A   A   N   D   N   D   D   D   P   T   T   T   V  33
125 CAT CCA ACA ACA ACC GAA CAA CCA GAT GAT AAA TTT GAA
     H   P   T   T   T   E   Q   P   D   D   K   F   E  46
164 TGT CCA AGT AGA TTT GGT TAT TTT GCC GAT CCA AAA GAT
     C   P   S   R   F   G   Y   F   A   D   P   K   D  59
203 CCA CAT AAA TTT TAT ATC TGT TCA AAT TGG GAA GCT GTA
     P   H   K   F   Y   I   C   S   N   W   E   A   V  72
242 CAT AAA GAT TGT CCA GGT AAT ACA CGA TGG AAT GAA GAT
     H   K   D   C   P   G   N   T   R   W   N   E   D  85
281 GAA GAA ACA TGC ACT TAAtaatgcaataaaattatgatttattatg
     E   E   T   C   T
327 gtaattcataaatcaacgttcaacaaaaaatcataaatttttattccaata
379 aattcattttatgttgtattacatgcttgtcaatttattacaaaataata
431 aaattatttatttacaaaaaaaaaaaaaaaaaaaaaaaaaaaa
```

Fig. 1

```
1   MANDNDDDPTTTVHPTTTEQPDDKFECPSRFGYFADPKDP   40
        NDDDPTTTV
           PTTTVHPTT
            TTTVHPTTT
             TTVHPTTTE
              TVHPTTTEQ
                 TTTEQPDDK
                  TTEQPDDKF

41  HKFYICSNWEAVHKDCPGNTRWNEDEETCT   70
        FYICSNWEA
         YICSNWEAVICSNWEAVH
          ICSNWEAVH
            SNWEAVHKD
               AVHKDCPGN
                     TRWNEDEET
```

HOUSE DUST MITE ALLERGEN

CROSS-REFERENCE TO RELATED APPLICATIONS

This application is a divisional of U.S. application Ser. No. 14/468,499 filed Aug. 26, 2014, abandoned, which is a continuation of U.S. application Ser. No. 12/298,901 filed Oct. 28, 2008, abandoned, which is a National Stage of PCT/AT2007/000201 filed Apr. 27, 2007 and claims the benefit of Austrian application A 733/2006 filed Apr. 28, 2006.

FIELD OF THE INVENTION

The present invention relates to a polypeptide having allergenic properties.

BACKGROUND OF THE INVENTION

More than 25% of the population in industrialised countries suffer from IgE-mediated allergies. Allergic patients are characterized by the increased production of IgE antibodies against per se harmless antigens (i.e., allergens). The immediate symptoms of Type I allergy (allergic rhinoconjunctivitis, asthma, dermatitis, anaphylactic shock) are caused by allergen-induced cross-linking of mast cell-bound IgE antibodies and the release of biologically active mediators (e.g., histamine, leukotriens).

House-dust mites (HDMs) represent one of the most important allergen sources worldwide. Almost 10% of the population and more than 50% of allergic patients are sensitized to mite allergens. The HDM *Dermatophagoides pteronyssinus* (Der p) is prevalent in Central Europe. The allergens of Der p comprise more than 30 proteins or glycoproteins of which twenty-one allergens have been characterized so far. Group 1 and 2 allergens (Der p 1 and Der p 2) represent the most important allergens from HDM, which are recognized by more than 80% of Der p allergic patients, but also other HDM allergens (e.g., Der p 5 and Der p 7) were shown to represent important Der p allergens despite a considerably lower IgE-binding frequency.

In Weghofer M. et al. (Clin Exp Allergy 35 (2005): 1384-1391) it was shown that recombinant dust mite allergens are able to inhibit IgE reactivity and hence may be used for diagnostic tests and therapy of Der p allergy.

In Pittner G. et al. (Clin Exp Allergy 34 (2004): 597-603) diagnostic test methods involving the major dust mite allergens Der p 1 and Der p 2 and highly cross-reactive dust mite allergens (for instance Der p 10) to be used for selection of patients for immunotherapy with Der p extracts were described.

In Vrtala S. et al. (Methods 32 (2004): 313-320) strategies for the production and evaluation of allergen derivatives exhibiting a reduced allergenic activity (e.g. hypo-energenic molecules) and suitable for vaccination are disclosed.

The EP 1 612 219 A1 deals with allergens derived from house-dust mites (Der p).

Crude HDM extracts, which are currently used for diagnosis and therapy of HDM allergic patients, are only standardized for Der p 1 and Der p 2, whereas other important allergens are only present in small amounts in HDM extracts.

SUMMARY OF THE INVENTION

It is an object of the present invention to provide novel polypeptides with allergenic and hypoallergenic properties which may be used in diagnosis, therapy and prevention of allergies, in particular of house dust mite allergy.

Therefore, the present invention relates to a polypeptide comprising an amino acid sequence having at least 60% identity to the amino acid sequence SEQ ID No. 1 or comprising at least one amino acid fragment of at least 6 consecutive amino acid residues of the amino acid sequence SEQ ID No. 1 or having immunological cross-reactivity to the amino acid sequence SEQ ID No. 1 or fragments thereof, wherein the amino acid sequence SEQ ID No. 1 codes for an allergen and the polypeptide comprises at least one T cell epitope recognized by a T cell receptor specific for a molecule having the amino acid sequence SEQ ID No. 1.

DETAILED DESCRIPTION OF THE INVENTION

The polypeptide with the amino acid sequence SEQ ID No. 1 (MKFNIIIVFI SLAILVHSSY AANDNDDDPT TTVHPTTTEQ PDDKFECPSR FGYFADPKDP HKFYIC-SNWE AVHKDCPGNT RWNEDEETCT) is a new major Der p allergen which may be useful, e.g., for diagnosis and therapy of Der p allergic patients. This new Der p allergen has a molecular weight of approximately 8 kDa and binds IgE from more than 50% of mite allergic patients.

The high IgE-binding frequency of the allergen with the amino acid sequence SEQ ID No. 1 and the observation that this allergen is biologically active makes it an important molecule for diagnosis of house dust mite allergy in an individual.

Furthermore, this new mite allergen is also useful for therapy or prevention of house dust mite allergy. The polypeptide according to the present invention induces high titers of specific IgG antibodies in mammals. If these specific IgG antibodies are administered to an individual, the exhibiting house dust mite allergen added to a sample, preferably serum, obtained from a house dust mite allergic individual, comprising IgE molecules of said individual IgE-binding to this new allergen is inhibited. This shows that allergen specific immunotherapy with this new mite allergen will induce blocking IgG antibodies in humans. The importance of the induction of blocking IgG antibodies for a successful immunotherapy has been shown recently in immunotherapy trials with defined allergens and allergen derivatives (Gafvelin, G., et al. (2005) Int Arch Allergy Immunol 138:59; Jutel, M., et al. (2005) J Allergy Clin Immunol 116:608). High levels of allergen-specific IgG antibodies were induced which inhibited allergen-induced basophil degranulation (Niederberger, V., et al. (2004) PNAS USA 101 Suppl 2:14677). Modifications of the polypeptide according to the present invention exhibiting allergenic properties leading to into hypoallergenic derivatives with reduced allergenic activity and preserved immunogenicity may further improve immunotherapy by the reduction of anaphylactic side effects (Valenta, R., et al. (2004) Adv Immunol 82:105). Hypoallergenic derivatives may be produced by molecular biological techniques or by the synthesis of peptides derived from the T-cell or B-cell epitopes of the allergen (Kyte, J., and R. F. Doolittle. (1982) J Mol Biol 157:105).

As used herein, a "polypeptide" refers to a molecule comprising at least 6 amino acid residues, preferably at least 8 amino acid residues.

The term "identity", as used herein, indicates whether any two (or more) peptide, polypeptide or protein sequences have amino acid sequences that are "identical" to a certain degree ("% identity") to each other. This degree can be determined using known computer algorithms such as the "FAST A" program, using for example, the default parameters as in Pearson et al. (1988) PNAS USA 85: 2444 (other programs include the GCG program package (Devereux, J., et al., Nucleic Acids Research (1984) Nucleic Acids Res., 12, 387-395), BLASTP, BLASTN, FASTA (Atschul, S. F., et al., J Molec Biol 215: 403 (1990); Guide to Huge Computers, Martin J. Bishop, ed., Academic Press, San Diego, 1994, and Carillo et al, (1988) SIAM J Applied Math 48: 1073). For instance, the BLAST tool of the NCBI database can be used to determine identity. Other commercially or publicly available programs include, DNAStar "MegAlign" program (Madison, Wis.) and the University of Wisconsin Genetics Computer Group (UWG) "Gap" program (Madison, Wis.)). Percent identity of protein molecules can further be determined, for example, by comparing sequence information using a GAP computer program (e.g. Needleman et al., (1970) J. Mol. Biol. 48:443, as revised by Smith and Waterman (1981) Adv. Appl. Math. 2:482). Briefly, the GAP program defines identity as the number of aligned symbols (i.e., nucleotides or amino acids) which are identical, divided by the total number of symbols in the shorter one of the two sequences. Default parameters for the GAP program can include: (1) a unary comparison matrix (containing a value of 1 for identities and for non-identities) and the weighted comparison matrix of Gribskov et al. 14:6745, as described by Schwartz and Dayhoff, eds., ATLAS OF PROTEIN SEQUENCE AND STRUCTURE, National Biomedical Research Foundation, pp. 353-358 (1979); (2) a penalty of 3.0 for each gap and an additional 0.10 penalty for each symbol in each gap; and (3) no penalty for end gaps.

According to a preferred embodiment of the present invention the amino acid sequence is at least 70%, preferably at least 80%, more preferably at least 90%, most preferably at least 95%, in particular 100%, identical to the amino acid sequence SEQ ID No. 1.

As used herein, "cross-reactivity" relates to the ability of an antibody to bind next to the antigen (e.g. peptide, protein, polypeptide), that did stimulate its production in an in vivo system, other antigens. This means that an antibody produced to bind specifically a polypeptide with the amino acid sequence SEQ ID No. 1 or fragments thereof may also show a binding affinity for a polypeptide which is not homologous to SEQ ID No. 1. The binding specificity of an antibody to a polypeptide can be determined by methods known in the art, e.g., ELISA, RIA, immunoblot etc. as described by Valenta et al. J Exp Med. (1992) 175: 377-385.

The polypeptide according to the present invention is preferably recombinantly produced by any method known in the art. The host in which said polypeptide may be produced can be of any kind by using corresponding vectors and plasmids (e.g. eukaryotic cells, preferably yeasts, mammalian cells, plant cells and insect cells, and prokaryotic cells, preferably *Escherichia coli* and *Bacillus subtilis*). Of course, it is also possible to produce the polypeptides of the present invention chemically by methods known in the art.

According to another preferred embodiment of the present invention said polypeptide is hypoallergenic.

As used herein, the term "hypoallergenic" refers to the ability of a peptide, polypeptide or protein derived from an allergen with allergenic properties to induce the production of antibodies specifically binding to said allergen and exhibiting reduced or no allergic reactions when administered to an individual. The reduced or missing ability of "hypoallergenic" derivatives of an allergen like SEQ ID No. 1 to induce an allergic reaction in an individual is obtained by removing or destroying the IgE binding epitopes from said allergens, however, by conserving the T cell epitopes present on said allergens. This can be achieved, for instance, by splitting the allergen in fragments with reduced or no IgE binding capacity and fusing some or all of said fragments in an order together which does not correspond to the order of the fragments in the wild type allergen (see e.g. EP 1 440 979). Another method for producing hypoallergenic" molecules from allergens involves C- and/or N-terminal deletions of the wild type allergen (see e.g. EP 1 224 215).

According to another preferred embodiment of the present invention said amino acid fragments are fused together in an order differing from the order of said fragments in SEQ ID No. 1.

The polypeptide according to the present invention may comprise amino acid fragments derived from SEQ ID No. 1 which may be preferably fused together in an order differing from the order in SEQ ID No. 1. This "shuffling" results in a polypeptide having altered features in respect to the wild type allergen having the amino acid sequence SEQ ID No. 1. For instance, this shuffling will result in an polypeptide comprising intact T cell epitopes and destroyed B cell epitopes. Such a molecule may have hypoallergenic properties.

Said at least one amino acid fragment, which substantially consists of a T cell epitope, is preferably selected from the group consisting of amino acid molecules comprising amino acids 5 to 13, 9 to 17, 10 to 18, 11 to 19, 12 to 20, 16 to 24, 17 to 25, 43 to 51, 44 to 52, 45 to 53, 47 to 55, 51 to 59 and 60 to 68 of SEQ ID No. 1.

In order to provoke a T cell immune response in an individual when administering a polypeptide according to the present invention said polypeptide has to comprise T cell epitopes. T cell epitopes comprise at least 6, preferably at least 7, more preferably at least 8, consecutive amino acid residues of SEQ ID No. 1. Said T cell epitopes may also be bound to a carrier via a or without a linker. Said carrier may be a solid support as used in microarray technology. The presence of T cell epitopes in a polypeptide can be determined by methods known in the art (see e.g. "Epitope Mapping: A practical approach" Ed. O. Westwood and F. Hay, 2001, Oxford University Press). A particularly preferred method is ELISpot (Tobey T W and Caulfield M J (2004), Methods Mol. Med. 94:121-132).

The identified T cell epitopes may be fused N- or C-terminally to other molecules like proteins or be part of a larger fragment obtained from SEQ ID No. 1 by fragmentation.

Another aspect of the present invention relates to a DNA molecule encoding a polypeptide according to the present invention.

Yet another aspect of the present invention relates to a vector comprising a DNA molecule according to the present invention.

Preferred vectors (e.g. plasmids) to be used according to the present invention are cloning as well as expression vectors comprising promoters, an origin of replication, regulatory elements, selection markers and/or other vector elements. If the vector is an integration vector able to be integrated into the genome of the host cell corresponding means may be provided on said vector (e.g. insertion sequence elements). The type of vector used and the regulatory elements present on said vector depend also into which host cell said vector will be integrated. If expression vectors are used the DNA molecule according to the present invention and encoding a polypeptide as described above, is operably linked to a promoter region.

Another aspect of the present invention relates to a cell transformed with a vector according to the present invention.

The cell to be used herein may be a eukaryotic as well as a prokaryotic cell. Preferred eukaryotic cells are yeast cells, in particular *Saccharomyces cerevisiae, Pichia pastoris* and *Hansenula polymorpha*, plant cells, in particular tobacco plant cells, insect cells and mammalian cells, like human and animal cells, in particular Chinese hamster ovary cells. Preferred prokaryotic cells are, e.g., *Bacillus subtilis* and *Escherichia coli*. A cell comprising a vector or a DNA molecule of the present invention may be used for producing a polypeptide according to the present invention.

Another aspect of the present invention relates to an anti-body binding to a polypeptide according to the present invention.

Antibodies according to the present invention include, but are not limited to, polyclonal, monoclonal, multispecific, humanized or chimeric antibodies, single chain antibodies, Fab fragments, F(ab') fragments and epitope-binding fragments of any of the above. Furthermore, antibodies are considered as being immunoglobulin molecules and immunologically active portions of immunoglobulin molecules, i.e., molecules that contain an antigen binding site that immunospecifically binds an antigen. The immunoglobulin molecules of the invention are preferably of the types IgG, IgM, IgD, IgA and IgY, class (e.g., IgG1, IgG2, IgG3, IgG4, IgA1 and IgA2) or subclass of immunoglobulin molecule.

Polyclonal antibodies can be prepared by administering a polypeptide of the invention, preferably using an adjuvant, to a non-human mammal and collecting the resultant antiserum. Improved titres can be obtained by repeated injections over a period of time. There is no particular limitation to the species of mammals which may be used for eliciting antibodies; it is generally preferred to use rabbits or guinea pigs, but horses, cats, dogs, goats, pigs, rats, cows, sheep, camels etc., can also be used. In the production of antibodies, a definite amount of immunogen of the invention is e.g. diluted with physiological saline solution to a suitable concentration and the resulting diluted solution is mixed with, e.g. complete Freund's adjuvant to prepare a suspension or with mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. The suspensions and mixtures are administered to mammals, e.g. intraperitoneally, e.g. to a rabbit, using from about 50 µg to about 2500 µg polypeptide of the invention per administration. The suspension is preferably administered about every two weeks over a period of up to about 2-3 months, preferably about 1 month, to effect immunization. Antibody is recovered by collecting blood from the immunized animal after the passage of 1 to 2 weeks subsequently to the last administration, centrifuging the blood and isolating serum from the blood.

Monoclonal antibodies may e.g. be of human or murine origin. Murine monoclonal antibodies may be prepared by the method of Köhler and Milstein (Köhler, G. and Milstein, C., Nature 256 (1975) 495), e.g. by fusion of spleen cells of hyperimmunized mice with an appropriate mouse myeloma cell line.

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. No. 5,807,715; U.S. Pat. No. 4,816,567 and U.S. Pat. No. 4,816,397.

Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modelling of the interactions of the CDR and framework residues to identify framework residues important for antigen binding and sequence comparison to identify unusual framework residues at particular positions (see, e.g., Queen et al., U.S. Pat. No. 5,585,089; Riechmann et al., Nature 332:323 (1988)). Antibodies can be humanized using a variety of techniques known in the art including, for example, CDR-grafting (EP 239,400; WO 91/09967; U.S. Pat. No. 5,225,539; U.S. Pat. No. 5,530,101; and U.S. Pat. No. 5,585,089), veneering or resurfacing (EP 592,106; EP 519,596; Padlan, Molecular Immunology 28 (4/5): 489-498 (1991); Studnicka et al., Protein Engineering 7(6): 805-814 (1994); Roguska. et al., PNAS 91:969-913 (1994)), and chain shuffling (U.S. Pat. No. 5,565,332).

The antibodies according to the present invention may advantageously be used for passive immunisation of an individual suffering from an allergy, in particular from house dust mite allergy. For passive immunisation the antibody is preferably an IgG or a derivative thereof (e.g. chimeric or humanized antibody). Furthermore this antibody may also be used for desensibilisation of an individual.

Another aspect of the present invention relates to a vaccine formulation comprising a polypeptide or an antibody according to the present invention.

Next to the polypeptide or the antibody the formulation according to the present invention may also comprise other substances like stabilisers, adjuvants, pharmaceutically acceptable carriers etc. Suitable protocols for the production of vaccine formulations are known to the person skilled in the art and can be found e.g. in "Vaccine Protocols" (A. Robinson, M. P. Cranage, M. Hudson; Humana Press Inc., U. S.; $2^{nd}$ edition 2003).

Yet another aspect of the present invention relates to the use of a polypeptide according to the present invention for the diagnosis of an allergy, in particular of house dust mite allergy, in an individual.

Said polypeptide may be used for diagnosis of allergy, in particular house dust mite allergy by exposing, e.g., a sample of an individual comprising histamine releasing cells to said polypeptide (see e.g. Purohit et al., Clin. Exp. Allergy 35 (2005): 186-192). Furthermore, the polypeptide(s) according to the present invention may be immobilised on a surface in order to form a polypeptide array/chip. Such arrays may be used, e.g., in high throughput screening in order to diagnose an allergy in a number of samples taken from a number of individuals.

Another aspect of the present invention relates to the use of a polypeptide or antibody according to the present invention for the preparation of a medicament for the immunotherapy of an allergy, in particular of house dust mite allergy.

The polypeptides and antibodies of the present invention can be used for active vaccination and passive vaccination respectively. Both can be used because the formation of protective IgGs is induced when a polypeptide of the present invention is administered to an individual and the administration of immunoglobulins directed to said polypeptide will lead to competition between IgE and administered protective antibodies which in turn alleviate the symptoms of the allergy.

Another aspect of the present invention relates to the use of a polypeptide according to any one of claims 1 to 4 or an antibody according to claim 7 for the preparation of a medicament for the prevention of an allergen sensitisation, in particular of house dust mite allergen sensitisation.

The polypeptide used for vaccination of an individual is preferably hypoallergenic. The use of such a polypeptide prevents the binding of IgE to said polypeptide and thus prevents an allergic reaction.

According to a preferred embodiment of the present invention said medicament further contains adjuvants, carrier, diluents, preservatives or mixtures thereof.

The medicament comprises preferably 10 ng to 1 g, more preferably 100 ng to 10 mg, especially 0.5 µg to 200 µg of said polypeptide.

BRIEF DESCRIPTION OF THE DRAWINGS

The present invention is further illustrated by the following figures and examples, however, without being restricted thereto.

FIG. 1 shows the cDNA and amino acid sequence of the clone 30-derived allergen. The start codon and the stop codon are underlined. The signal sequence comprises amino acid residues 1 to 21 with the predicted cleavage site between amino acid residues 21 (A) and 22 (A) in bold. The numbers on the left side of the sequence indicate the nucleotide positions and the numbers on the right side of the sequence the amino acid positions.

FIG. 2B, MS analysis of the purified clone 30-derived allergen shows the mass/charge ratio on the x-axis and the signal intensity on the y-axis as the percentage of the most intense signal obtained in the investigated mass range. The peak at 7979.20 corresponds to the calculated mass of the deduced amino acid sequence of the clone 30-derived allergen.

EXAMPLES

The present examples describe the identification of a new major Der p allergen which may be useful, e.g., for diagnosis and therapy of Der p allergic patients.

The cDNA coding for this new mite allergen was isolated from a Der p expression cDNA library and expressed in *Escherichia coli* (*E. coli*) as recombinant allergen. The new allergen has a molecular weight of approximately 8 kDa and binds IgE from more than 50% of mite allergic patients, thus representing a major allergen.

Example 1: Expression and Purification of the Clone 30-Derived Allergen

Figures 2A, 2B:
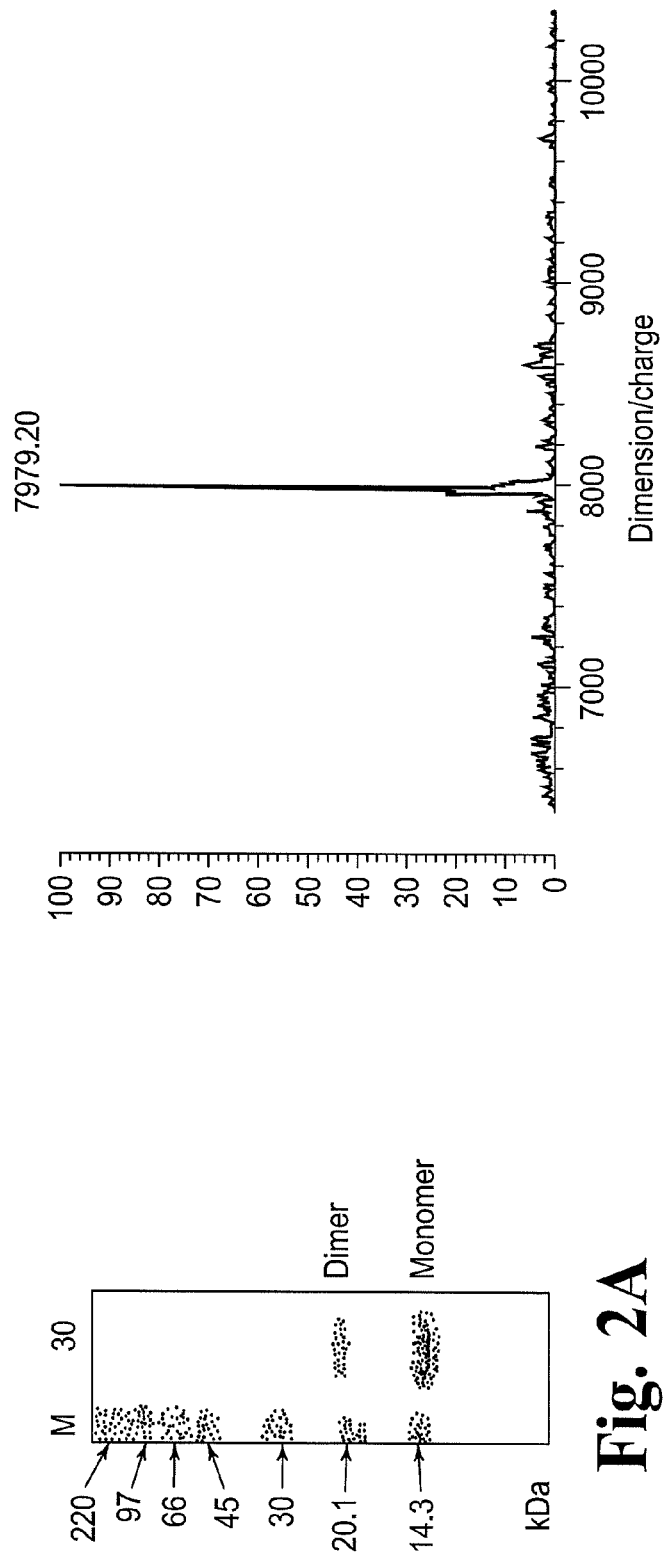
FIG. 2A shows a Coomassie Blue staining of the clone 30-derived allergen and FIG. 2B shows mass spectroscopy (MS) of the clone 30-derived allergen. FIG. A, The Coomassie Blue stained SDS-PAGE gel displays a molecular weight marker (M) and 3 µg of purified clone 30-derived allergen (30).

The cDNA sequence of clone 30 (FIG. 1) coding for the predicted mature clone 30-derived allergen (nucleotides 89-295 with an additional ATG at the N-terminus) was subcloned into the expression vector pET-17b (Novagene, WI) and expressed in *Escherichia coli* BL21 (DE3) cells (Stratagene, CA). The bacterial cells were grown overnight in LB-medium containing 100 mg/L ampicillin at 27° C. and expression of the recombinant protein was induced by adding isopropyl-β-thiogalactopyranoside (IPTG) to a final concentration of 0.5 mM. After cultivation for additional 6 hours at 27° C., cells from 1 liter *E. coli* culture were harvested by centrifugation (15 min, 3,000 rpm, 4° C., Sorvall RCSC) and pellets were resuspended in 30 ml 25 mM Imidazole pH 7.4/0.1% (v/v) Triton X 100. Afterwards the bacterial cells were treated with 300 µg lysozyme for 20 min at room temperature. The lysate of the bacterial cells was thrice frozen in liquid nitrogen and defrosted in a 50° C. waterbath. The genomic DNA was degraded by addition of 3 µg DNase for 10 min at room temperature followed by the addition of 600 µl 5M NaCl. These lysed bacterial cells were centrifuged at 18,000 rpm, 20 min, 4° C. and proteins of the soluble fraction containing the clone 30-derived allergen were treated with 60% ammonium sulphate for 1.5 hours at 4° C. Precipitated proteins were separated by centrifugation (18,000 rpm, 20 min, 4° C.) and the soluble fraction containing the clone 30-derived allergen was dialyzed against 2M ammonium sulphate/50 mM sodium phosphate pH 7.0/10 mg/L phenylmethylsulphonylfluoride (PMSF) and applied to a HiTrap Phenyl FF (high sub) column (Amersham Biosciences AB, Sweden). The clone 30-derived allergen was eluted by a 500-0 mM ammonium sulphate gradient and fractions containing the clone 30-derived allergen were pooled. After dialysis against 20 mM Tris-Cl pH 8.0/10 mg/L PMSF, the sample was applied to a HiTrap DEAE Sepharose FF column (Amersham Biosciences). The clone 30-derived allergen was eluted by a 0-500 mM NaCl gradient and fractions containing more than 90% pure clone 30-derived allergen were pooled. The clone 30-derived allergen was dialysed against 20 mM Tris-Cl pH 8.0 and stored at −20° C. A protein sample was analyzed for purity by 14% sodium dodecyl sulfate-polyacrylamide gel electrophoresis (SDS-PAGE) and Coomassie brilliant blue protein staining (FIG. 2 A). Molecular mass analysis of the mature protein depicted a mass of 7.98 kDa (FIG. 2 B) which corresponds to the calculated mass of the deduced amino acid sequence of the clone 30-derived allergen although in SDS-PAGE the protein runs at approximately 14 kDa (FIG. 2A).

Example 2: IgE Reactivity of the Clone 30-Derived Allergen

Figure 3:
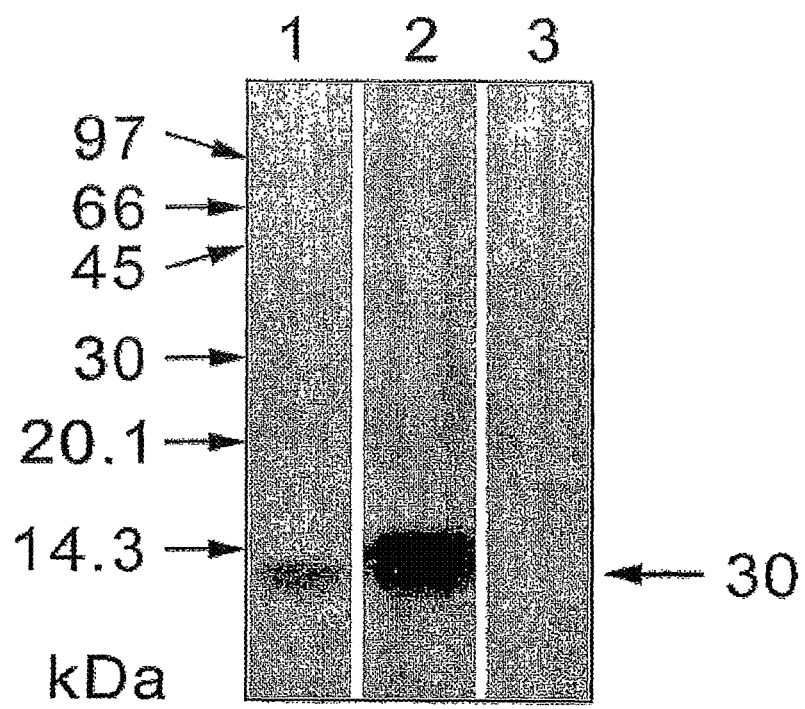
FIG. 3 shows an immunoblot of the clone 30-derived allergen. Samples of the purified clone 30-derived allergen were separated by SDS-PAGE, blotted onto nitrocellulose and incubated with sera from two mite allergic patients (1, 2) and one serum from a non-allergic individual (3). Bound IgE antibodies specific for the clone 30-derived allergen were detected with $^{125}$I-labeled anti-human IgE antibodies.

The IgE binding capacity of the clone 30-derived allergen was demonstrated by immunoblot analysis using two sera of *Dermatophagoides pteronyssinus* sensitized individuals (FIG. 3). Samples of the clone 30-derived allergen were separated by SDS-PAGE and blotted onto nitrocellulose. Nitrocellulose strips were incubated with 1:10 diluted human sera (1-3) and bound IgE antibodies were detected with 1:10 diluted $^{125}$I-labelled anti-human IgE antibodies. The sera of the mite allergic patients (1, 2) reacted specifically with the clone 30-derived allergen. The control serum from a non-allergic individual (3) did not react with the clone 30-derived allergen.

The frequency of IgE binding was determined in an ELISA assay with sera from 53 mite allergic individuals with perennial symptoms indicative for mite allergy, positive SPT and *D. pteronyssinus* specific IgE-RAST. An ELISA plate (Nunc, Denmark) was coated with 5 µg/ml clone 30-derived allergen and incubated with 1:10 diluted sera from mite allergic patients. Human IgE binding was detected with 1:1000 diluted AKP-conjugated anti-human IgE antibodies (BD Biosciences-Pharmingen, NJ).

Twenty-nine out of 53 sera from mite allergic patients (55%) showed IgE reactivity to the clone 30-derived allergen (Table I).

TABLE I

| IgE binding frequency of clone 30-derived allergen | | |
|---|---|---|
| Recombinant protein | Number of patients with IgE reactivity | Percentage of IgE reactivity |
| Clone 30-derived allergen | 29 (n = 53) | 55 |

Example 3: Immunization with the Clone 30-Derived Allergen Induces IgG Antibodies in Rabbits In order to test whether the clone 30-derived allergen is immunogenic, a rabbit was immunized with the new allergen using Freund's adjuvant. The rabbit was immunized 3 times with 200 µg protein/injection using once Freund's complete and twice incomplete adjuvants (Charles River, Germany).

The induction of IgG antibodies was studied by dot blot experiments. Recombinant Der p 2 and the clone 30-derived allergen were dotted onto nitrocellulose strips (0.5 µg/dot) and the strips were incubated with 1:1000, 1:10,000, 1:100,000 and 1:1,000,000 diluted rabbit preimmune serum and anti-clone 30-derived allergen antiserum. Bound IgG antibodies were detected with $^{125}$I-labelled anti-rabbit whole antibodies from donkey (Amersham).

Figure 4:
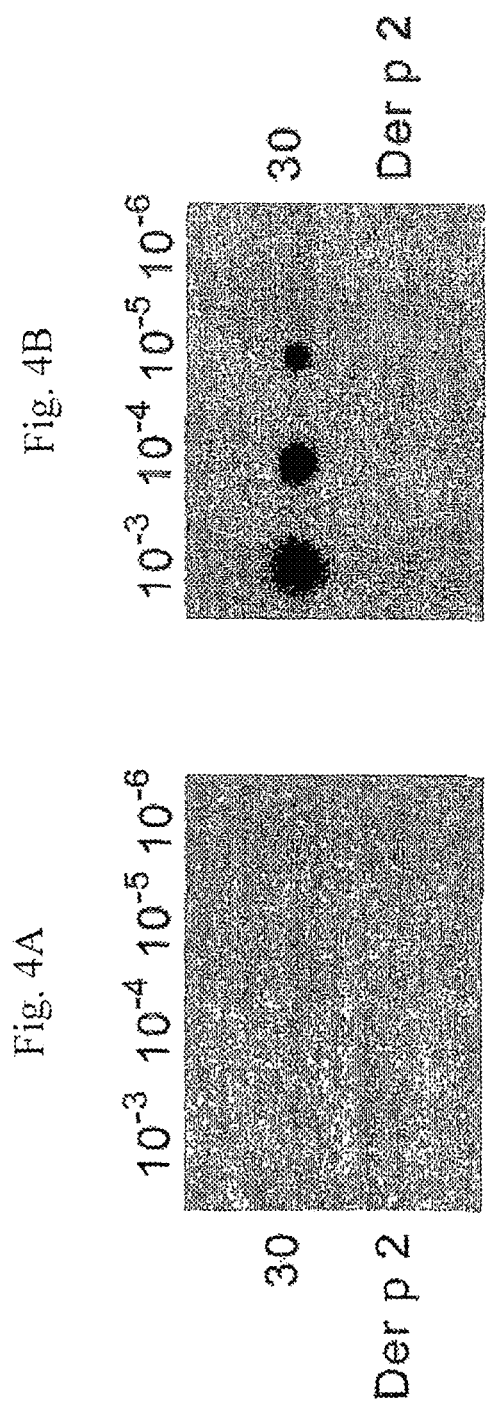
FIGS. 4A and B show the IgG reactivity of a rabbit anti-clone 30-derived allergen antiserum. The clone 30-derived allergen and the major mite allergen, Der p 2, were dotted onto nitrocellulose strips and incubated with 1:1000-1:1,000,000 diluted rabbit preimmune serum in FIG. 4A or rabbit anti-clone 30-derived allergen antiserum in FIG. 4B. Bound IgG antibodies were detected with $^{125}$I-labelled anti-rabbit whole antibodies from donkey.

High titers of specific IgG antibodies were induced with the clone 30-derived allergen (FIG. 4). The anti-clone 30-derived allergen antiserum reacted specifically with the clone 30-derived allergen up to a dilution of 1:100,000 and no reaction with Der p 2 was observed (FIG. 4 B). The preimmune serum did not react with the clone 30-derived allergen and Der p 2 (FIG. 4 A).

Example 4: IgG Antibodies Induced with the Clone 30-Derived Allergen in Rabbits Block Mite Allergic Patients IgE Binding to Clone 30-Derived Allergen The ability of rabbit antibodies specific for the clone 30-derived allergen to block the binding of patients' IgE to the allergen was examined by ELISA-inhibition assays. ELISA plate-bound clone 30-derived allergen (5 µg/ml) was preincubated with 1:100 in PBST/0.5% (w/v) BSA diluted rabbit anti-clone 30-derived allergen antibodies or rabbit preimmune serum and incubated at 4° C. overnight. Subsequently, the plate was exposed to 1:5 in PBST/0.5% (w/v) BSA diluted sera from 14 mite allergic patients overnight at 4° C. Bound IgE antibodies were detected with HRP-coupled goat anti-human IgE antibodies (Kirkegaard & Perry Gaithersbury, MD) diluted 1:2500 in PBST/0.5% BSA. The degree of inhibition was calculated as follows: % inhibition of IgE binding=100-OD$_{anti-clone}$ 30-derived serum×100/OD$_{preimmune\ serum}$.

For the majority of patients a strong inhibition of IgE binding, ranging from 25 to 97% (mean: 82%) could be observed (Table II). In half of the sera, the IgE binding to clone 30-derived allergen was inhibited 90% or more.

Table II. Rabbit anti-clone 30 derived IgG antibodies inhibit IgE binding from mite allergic patients' sera to the clone 30-derived allergen

TABLE II

| Rabbit anti-clone 30 derived IgG antibodies inhibit IgE binding from mite allergic patients' sera to the clone 30-derived allergen | | | | | | | | |
|---|---|---|---|---|---|---|---|---|
| | Patient number | | | | | | | |
| Preincubation with | 1 | 2 | 3 | 4 | 5 | 6 | 7 | 8 |
| Preimmune serum (OD values) | 0.009 | 1.140 | 0.461 | 0.982 | 2.620 | 0.628 | 0.790 | 0.347 |
| Anti-clone 30-derived serum (OD values) | 0.080 | 0.083 | 0.070 | 0.155 | 0.220 | 0.039 | 0.071 | 0.101 |
| % inhibition of IgE binding | 90 | 83 | 85 | 84 | 91 | 94 | 91 | 71 |

| | Patient number | | | | | | |
|---|---|---|---|---|---|---|---|
| Preincubation with | 9 | 10 | 11 | 12 | 13 | 14 | mean |
| Preimmune serum (OD values) | 0.484 | 0.288 | 0.583 | 1.533 | 1.635 | 1.036 | 0.010 |
| Anti-clone 30-derived serum (OD values) | 0.029 | 0.078 | 0.416 | 0.047 | 0.362 | 0.137 | 0.133 |
| % inhibition of IgE binding | 94 | 71 | 25 | 97 | 78 | 87 | 82 |

Example 5: The Clone 30-Derived Allergen is Biologically Active

The upregulation of CD203c on basophils can be used as marker for induced activation and subsequent degranulation of basophils and therefore for the determination of the allergenic activity of an allergen. Heparinized blood samples (100 μl) from a mite allergic patient were incubated with various concentrations of the clone 30-derived allergen, a monoclonal anti-IgE antibody (Immunotech, France) or PBS for 15 minutes at 37° C. CD203c expression was determined by two-color flow cytometry on a FACScan (Becton Dickinson, CA).

Figure 5:
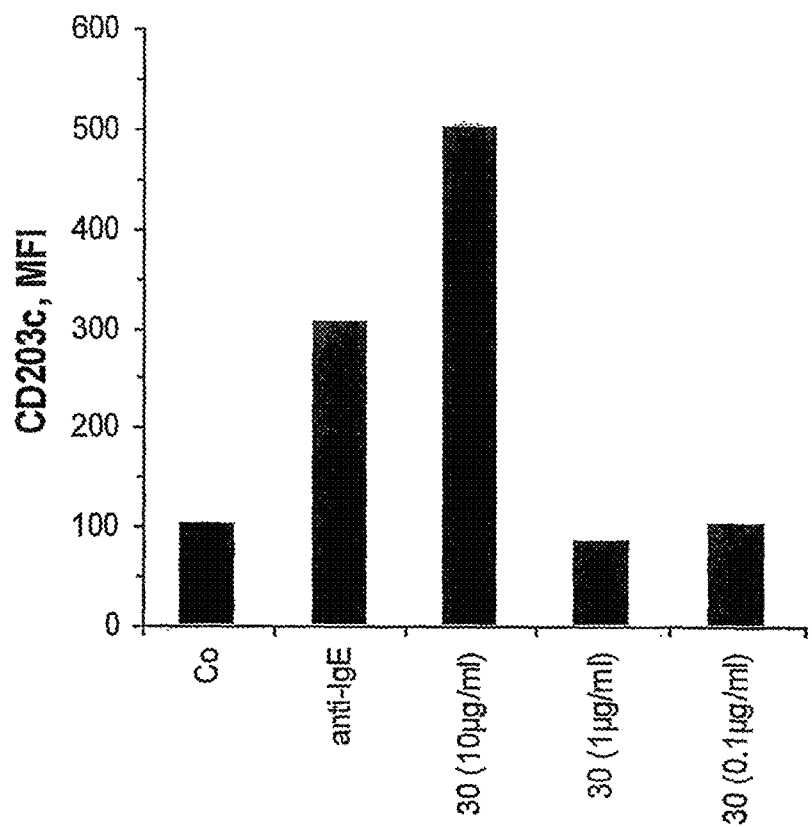
FIG. 5 shows the biological activity of the clone 30-derived allergen. Blood samples from a mite allergic patient were exposed to 10 µg/ml, 1 µg/ml and 0.1 µg/ml of clone 30-derived allergen, to 1 µg/ml anti-IgE antibodies or to PBS as buffer control (Co) (x-axis). CD203c expression was determined by FACS analysis and is displayed as mean fluorescence index (MFI) (y-axis).

The clone 30-derived allergen induced upregulation of CD203c expression on basophils of a mite allergic patient at a concentration of 10 μg/ml (FIG. 5). Anti-human IgE antibodies (positive control) induced upregulation of CD203c expression at 1 μg/ml, whereas with the negative control (PBS alone) no upregulation was obtained.

Example 6: Surface-Exposed Regions and Possible T-Cell Epitopes of the Clone 30-Derived Allergen The hydrophilic regions of a protein are likely to be exposed on the surface of the molecule and may potentially be antigenic. Therefore, the hydrophilic regions on the surface of the clone 30-derived allergen may represent potential B-cell epitopes. ProtScale (http://www.expasy.org/tools/protscale.html) allows the computation and presentation of the hydrophobicity profile (Kyte & Doolittle) produced by any amino acid scale of the protein 30-derived allergen. A window size of 7 was chosen for the structural investigation. The ProtScale output of the mature clone 30-derived allergen shows a protein with lots of negative peaks representing hydrophilic segments (FIG. 6 A). B-cell epitopes of the clone 30-derived allergen are located between amino acids 3-12, 15-28, 34-43 and 49-68 of the mature protein.

Figures 6A, 6B:
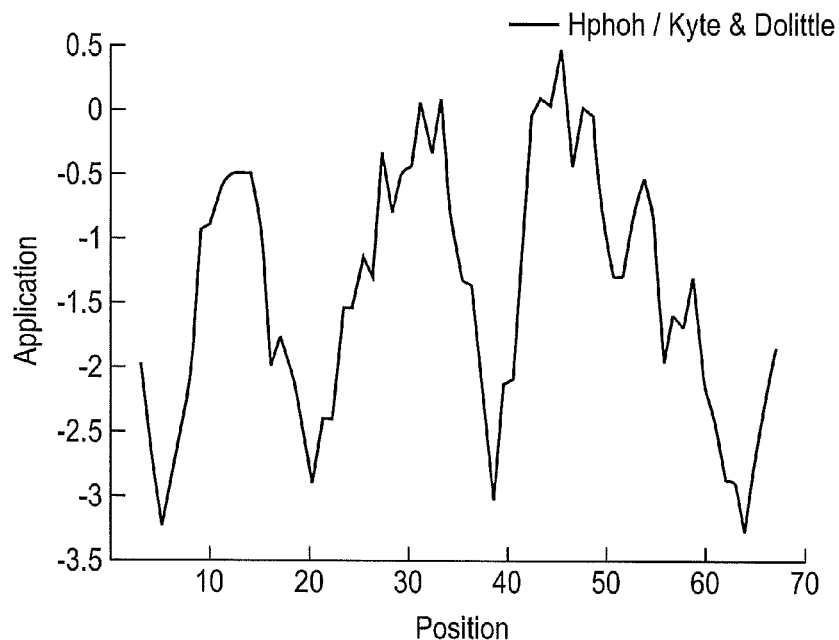
FIG. 6A shows an analysis of the hydrophobicity (Kyte & Doolittle) of the mature clone 30-derived allergen using ProtScale. The amino acid positions of the mature protein including an N-terminal methionin are displayed on the x-axis.
FIG. 6B shows the prediction of possible T-cell epitopes of the clone 30-derived allergen with MULTI-PRED, a web-based computational system. Numbers on each side of the sequence indicate the amino acid positions of the mature clone 30-derived allergen.

T-cells of the human immune system recognize allergens as short peptide fragments (T-cell epitopes) derived from the degradation of the allergens. MULTIPRED (http://antigen.i2r.astar.edu.sg/multipred/) is a web-based computational system for the prediction of peptides which bind to multiple molecules belonging to the human leukocyte antigen (HLAs; human MHC, major histocompatibility complex) alleles. The predicted results for individual 9 mer peptides with a 'Sum' (the sum of the individual binding scores of the peptide to the MHC molecules) over 40 are shown in FIG. 6B. T-cell epitopes are located near the N- and the C-terminus of the mature clone 30-derived allergen.

---

The invention claimed is:

1. An immobilized polypeptide comprising a polypeptide bound to a surface of a polypeptide array or a chip, wherein the polypeptide consists of the amino acid sequence of SEQ ID NO:1, SEQ ID NO:3, SEQ ID NO:1 lacking the N-terminal methionine, SEQ ID NO:3 lacking the N-terminal methionine, or a combination thereof.

2. The immobilized polypeptide of claim 1, wherein the polypeptide consists of the amino acid sequence of SEQ ID NO: 1.

3. The immobilized polypeptide of claim 1, wherein the polypeptide consists of the amino acid sequence of SEQ ID NO:3.

4. The immobilized polypeptide of claim 1, wherein the polypeptide consists of the amino acid sequence of SEQ ID NO:1 lacking the N-terminal methionine.

5. The immobilized polypeptide of claim 1, wherein the polypeptide consists of the amino acid sequence of SEQ ID NO:3 lacking the N-terminal methionine.

* * * * *

SEQUENCE LISTING

```
<160> NUMBER OF SEQ ID NOS: 16

<210> SEQ ID NO 1
<211> LENGTH: 90
<212> TYPE: PRT
<213> ORGANISM: Dermatophagoides pteronyssinus

<400> SEQUENCE: 1

Met Lys Phe Asn Ile Ile Val Phe Ile Ser Leu Ala Ile Leu Val
1               5                   10                  15

His Ser Ser Tyr Ala Ala Asn Asp Asn Asp Asp Pro Thr Thr Thr
                20                  25                  30

Val His Pro Thr Thr Thr Glu Gln Pro Asp Asp Lys Phe Glu Cys Pro
            35                  40                  45

Ser Arg Phe Gly Tyr Phe Ala Asp Pro Lys Asp Pro His Lys Phe Tyr
    50                  55                  60

Ile Cys Ser Asn Trp Glu Ala Val His Lys Asp Cys Pro Gly Asn Thr
65                  70                  75                  80

Arg Trp Asn Glu Asp Glu Glu Thr Cys Thr
                85                  90

<210> SEQ ID NO 2
<211> LENGTH: 472
<212> TYPE: DNA
<213> ORGANISM: Dermatophagoides pteronyssinus

<400> SEQUENCE: 2
caatattttc tgcttgtttt tgaaaatgaa attcaacata atcatcgttt ttatttcgtt      60
ggccattttg gtccattcat catatgccgc caatgataat gatgatgatc ctaccacaac     120
cgttcatcca acaacaaccg aacaaccaga tgataaattt gaatgtccaa gtagatttgg     180
ttattttgcc gatccaaaag atccacataa attttatatc tgttcaaatt gggaagctgt     240
acataaagat tgtccaggta atacgatg gaatgaagat gaagaaacat gcacttaata     300
atgcaataaa attatgattt attatggtaa ttcataaatc aacgttcaac aaaaaatcat     360
```

-continued

```
aaattttat tccaataaat tcattttat gttgtattac atgcttgtca atttattaca    420
aaataataaa attatttatt tacaaaaaaa aaaaaaaaaa aaaaaaaaaa aa          472

<210> SEQ ID NO 3
<211> LENGTH: 70
<212> TYPE: PRT
<213> ORGANISM: Dermatophagoides pteronyssinus

<400> SEQUENCE: 3

Met Ala Asn Asp Asn Asp Asp Pro Thr Thr Thr Val His Pro Thr
1               5                   10                  15

Thr Thr Glu Gln Pro Asp Asp Lys Phe Glu Cys Pro Ser Arg Phe Gly
            20                  25                  30

Tyr Phe Ala Asp Pro Lys Asp Pro His Lys Phe Tyr Ile Cys Ser Asn
        35                  40                  45

Trp Glu Ala Val His Lys Asp Cys Pro Gly Asn Thr Arg Trp Asn Glu
    50                  55                  60

Asp Glu Glu Thr Cys Thr
65                  70

<210> SEQ ID NO 4
<211> LENGTH: 9
<212> TYPE: PRT
<213> ORGANISM: Artificial Sequence
<220> FEATURE:
<223> OTHER INFORMATION: T-cell epitope of the Dermatophagoides
      pteronyssinus allergen

<400> SEQUENCE: 4

Asn Asp Asp Asp Pro Thr Thr Thr Val
1               5

<210> SEQ ID NO 5
<211> LENGTH: 9
<212> TYPE: PRT
<213> ORGANISM: Artificial Sequence
<220> FEATURE:
<223> OTHER INFORMATION: T-cell epitope of the Dermatophagoides
      pteronyssinus allergen

<400> SEQUENCE: 5

Pro Thr Thr Thr Val His Pro Thr Thr
1               5

<210> SEQ ID NO 6
<211> LENGTH: 9
<212> TYPE: PRT
<213> ORGANISM: Artificial Sequence
<220> FEATURE:
<223> OTHER INFORMATION: T-cell epitope of the Dermatophagoides
      pteronyssinus allergen

<400> SEQUENCE: 6

Thr Thr Thr Val His Pro Thr Thr Thr
1               5

<210> SEQ ID NO 7
<211> LENGTH: 9
<212> TYPE: PRT
<213> ORGANISM: Artificial Sequence
<220> FEATURE:
<223> OTHER INFORMATION: T-cell epitope of the Dermatophagoides
      pteronyssinus allergen
```

```
<400> SEQUENCE: 7

Thr Thr Val His Pro Thr Thr Thr Glu
1               5

<210> SEQ ID NO 8
<211> LENGTH: 9
<212> TYPE: PRT
<213> ORGANISM: Artificial Sequence
<220> FEATURE:
<223> OTHER INFORMATION: T-cell epitope of the Dermatophagoides
      pteronyssinus allergen

<400> SEQUENCE: 8

Thr Val His Pro Thr Thr Thr Glu Gln
1               5

<210> SEQ ID NO 9
<211> LENGTH: 9
<212> TYPE: PRT
<213> ORGANISM: Artificial Sequence
<220> FEATURE:
<223> OTHER INFORMATION: T-cell epitope of the Dermatophagoides
      pteronyssinus allergen

<400> SEQUENCE: 9

Thr Thr Thr Glu Gln Pro Asp Asp Lys
1               5

<210> SEQ ID NO 10
<211> LENGTH: 9
<212> TYPE: PRT
<213> ORGANISM: Artificial Sequence
<220> FEATURE:
<223> OTHER INFORMATION: T-cell epitope of the Dermatophagoides
      pteronyssinus allergen

<400> SEQUENCE: 10

Thr Thr Glu Gln Pro Asp Asp Lys Phe
1               5

<210> SEQ ID NO 11
<211> LENGTH: 9
<212> TYPE: PRT
<213> ORGANISM: Artificial Sequence
<220> FEATURE:
<223> OTHER INFORMATION: T-cell epitope of the Dermatophagoides
      pteronyssinus allergen

<400> SEQUENCE: 11

Phe Tyr Ile Cys Ser Asn Trp Glu Ala
1               5

<210> SEQ ID NO 12
<211> LENGTH: 9
<212> TYPE: PRT
<213> ORGANISM: Artificial Sequence
<220> FEATURE:
<223> OTHER INFORMATION: T-cell epitope of the Dermatophagoides
      pteronyssinus allergen

<400> SEQUENCE: 12

Tyr Ile Cys Ser Asn Trp Glu Ala Val
1               5
```

```
<210> SEQ ID NO 13
<211> LENGTH: 9
<212> TYPE: PRT
<213> ORGANISM: Artificial Sequence
<220> FEATURE:
<223> OTHER INFORMATION: T-cell epitope of the Dermatophagoides
      pteronyssinus allergen

<400> SEQUENCE: 13

Ile Cys Ser Asn Trp Glu Ala Val His
1               5

<210> SEQ ID NO 14
<211> LENGTH: 9
<212> TYPE: PRT
<213> ORGANISM: Artificial Sequence
<220> FEATURE:
<223> OTHER INFORMATION: T-cell epitope of the Dermatophagoides
      pteronyssinus allergen

<400> SEQUENCE: 14

Ser Asn Trp Glu Ala Val His Lys Asp
1               5

<210> SEQ ID NO 15
<211> LENGTH: 9
<212> TYPE: PRT
<213> ORGANISM: Artificial Sequence
<220> FEATURE:
<223> OTHER INFORMATION: T-cell epitope of the Dermatophagoides
      pteronyssinus allergen

<400> SEQUENCE: 15

Ala Val His Lys Asp Cys Pro Gly Asn
1               5

<210> SEQ ID NO 16
<211> LENGTH: 9
<212> TYPE: PRT
<213> ORGANISM: Artificial Sequence
<220> FEATURE:
<223> OTHER INFORMATION: T-cell epitope of the Dermatophagoides
      pteronyssinus allergen

<400> SEQUENCE: 16

Thr Arg Trp Asn Glu Asp Glu Glu Thr
1               5
```